US00PP18091P2

(12) United States Plant Patent
Goffreda et al.

(10) Patent No.: US PP18,091 P2
(45) Date of Patent: Sep. 25, 2007

(54) PEACH TREE NAMED 'NJ352'

(50) Latin Name: ***Prunus persica* L.**
Varietal Denomination: NJ352

(75) Inventors: Joseph C. Goffreda, Manalapan, NJ (US); Anna M. Voordeckers, East Windsor, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 0 days.

(21) Appl. No.: 11/392,118

(22) Filed: Mar. 29, 2006

(51) Int. Cl.
*A01H 5/00* (2006.01)

(52) U.S. Cl. ..... Plt./198

(58) Field of Classification Search ..... Plt./198
See application file for complete search history.

*Primary Examiner*—Anne Marie Grunberg
*Assistant Examiner*—S. B. McCormick-Ewoldt
(74) *Attorney, Agent, or Firm*—Michael J. Medley; Driggs, Hogg & Fry Co., L.P.A.

(57) ABSTRACT

A new and distinct peach variety of *Prunus persica* named 'NJ352' is provided. This variety is distinguished from other peach varieties by its unique combination of nonshowy flowers, fruit that ripen in latter part of mid-season, attractive fruit with a yellow-orange ground color, freestone fruit with a juicy, melting texture and moderately acidic flavor, and good production of firm fruit.

6 Drawing Sheets

Latin name of genus and species of the plant claimed: *Prunus persica* L.
Variety denomination: 'NJ352'.

BACKGROUND OF THE INVENTION

The present invention relates to a new and distinct variety of peach tree named 'NJ352'. Our new tree resulted from crossing 'D90-9' as the seed parent with 'NJ318' peach tree, as the pollen parent. The new variety differs from seed parent 'D90-9' (unpatented) in that the new variety has small, nonshowy flowers and fruit that ripen in the latter part of mid-season, while the seed parent has large, showy flowers and fruit that do not ripen during a typical growing season. The new variety differs from pollen parent 'NJ318' (unpatented) in that the new variety has fruit with yellow-orange flesh and moderate acidity, while the pollen parent has fruit with white flesh and low acidity. The resulting tree was selected when growing in a cultivated area as the 162$^{nd}$ tree in the 101$^{st}$ row of Block D at the Rutgers Fruit research and Extension Center in Cream Ridge, N.J.

BRIEF SUMMARY OF THE INVENTION

The 'NJ352' variety is distinguished from other peach varieties due to the following unique combination of characteristics:

- Attractive round fruit with a slightly depressed apex point.
- Fruit with an attractive yellow-orange ground color.
- Good production of firm fruit.
- Fruit has better than average eating quality.

The variety was asexually reproduced at the Rutgers Fruit Research and Extension Center in Cream Ridge, N.J. Asexual reproduction of this new variety by budding onto 'Lovell' rootstock (unpatented) shows that the foregoing characteristics are so reproduced.

The following detailed description concerns the original tree, 'NJ352'. The original tree and asexual progeny have been observed growing in a cultivated area in Cream Ridge, N.J. Certain characteristics of this variety, such as growth and color, may change with changing environmental conditions (such as, light, temperature, moisture, nutrient availability) or other factors. Color descriptions and other terminology are used in accordance with their ordinary dictionary descriptions, unless the context clearly indicates otherwise. Color designations are made with reference to The Royal Horticultural Society (R.H.S.) Colour Chart.

BRIEF DESCRIPTION OF THE DRAWINGS

This new variety is illustrated by the accompanying photographic drawings, depicting the peach tree by the best possible color representation using color photography. Colors are approximate as color depends on horticultural practices, such as light level, fertilization rate, and other conditions and, therefore, the color characteristics of this new variety should be determined with reference to the observations described herein, rather than from these illustrations alone.

Figure 1:
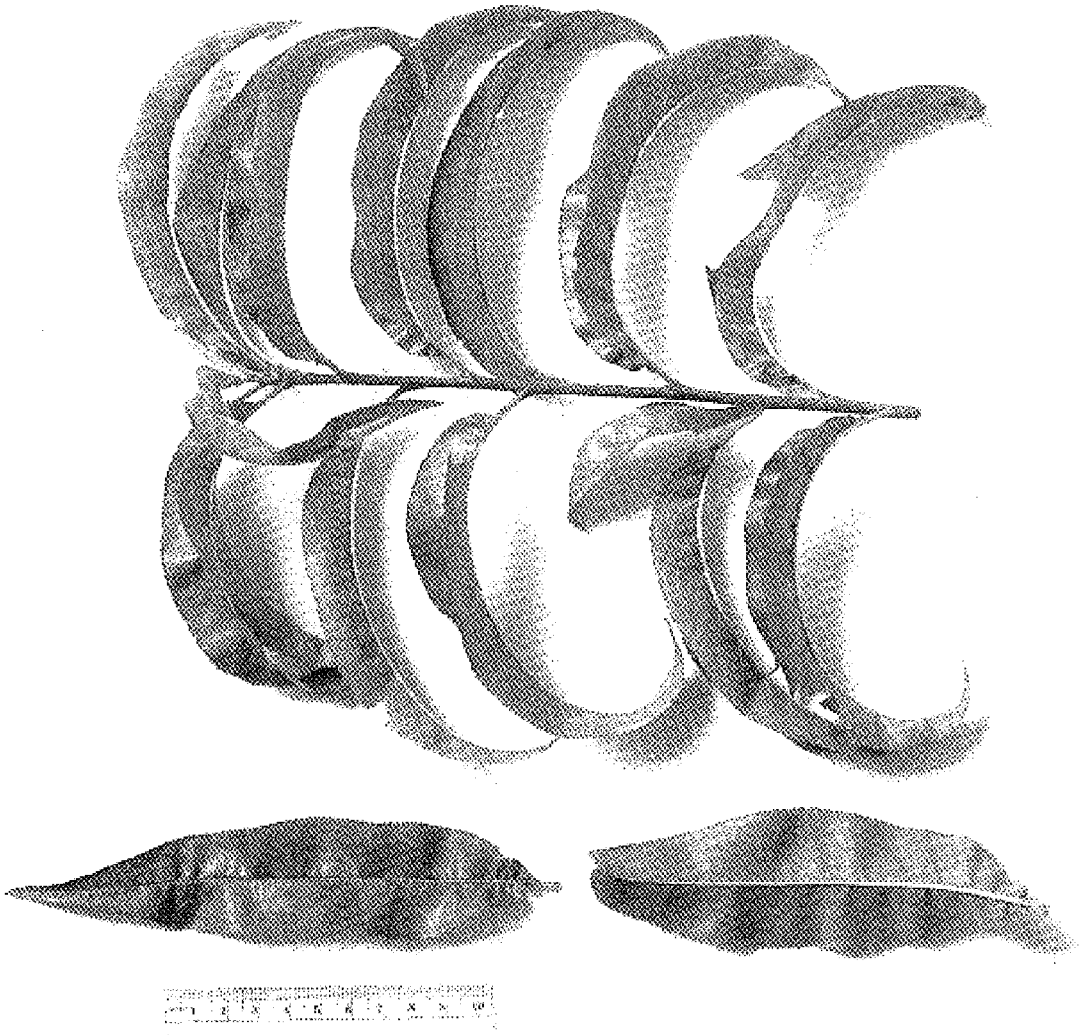
FIG. 1 is a color photograph taken on Aug. 29, 2005 of a characteristic twig of 'NJ352' in late summer bearing typical leaves of the mature foliage.
Figure 2:
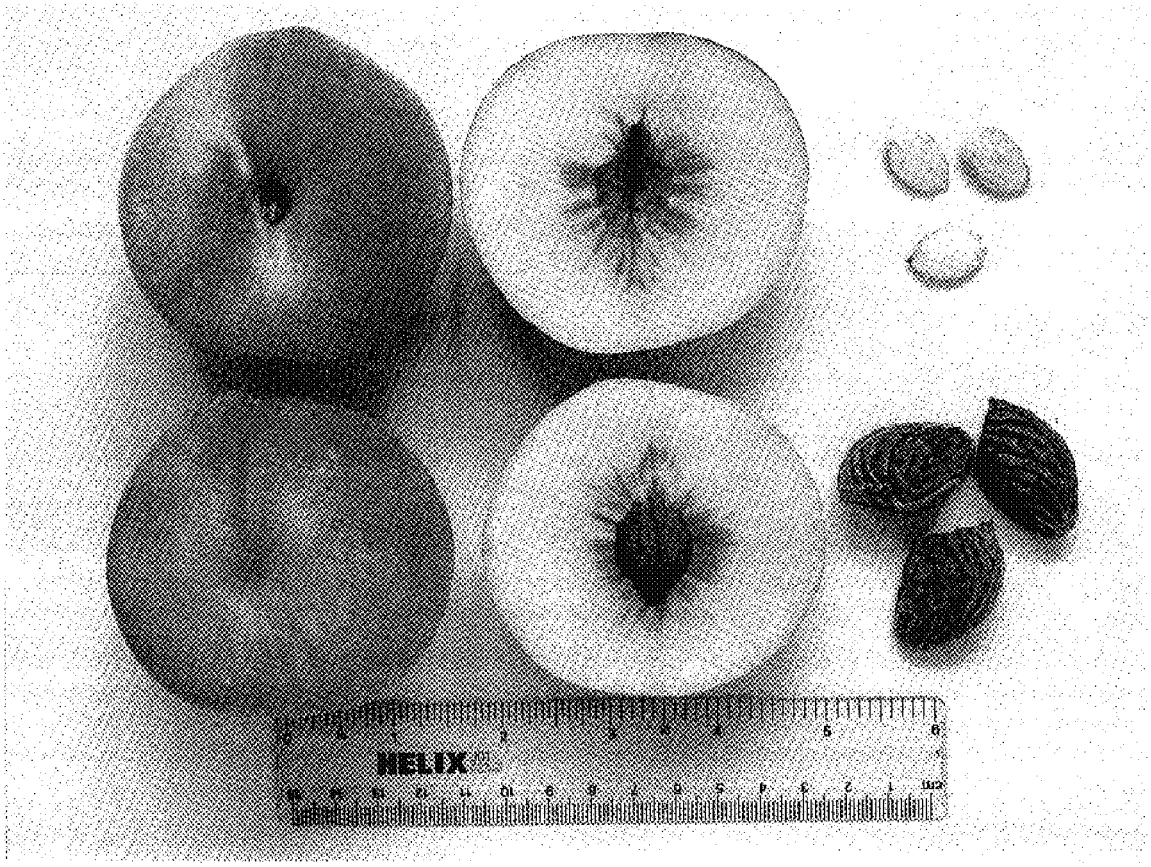
FIG. 2 is a color photograph of mature fruit of 'NJ352' and stones harvested in Cream Ridge, N.J. on Aug. 25, 2004. Whole fruit are presented in two positions and a transverse cross section to show that the pericarp does not adhere to the pit when the fruit is mature. The stones illustrate the obovoid shape and the pit grooves on the surface of the stone.
Figure 3:
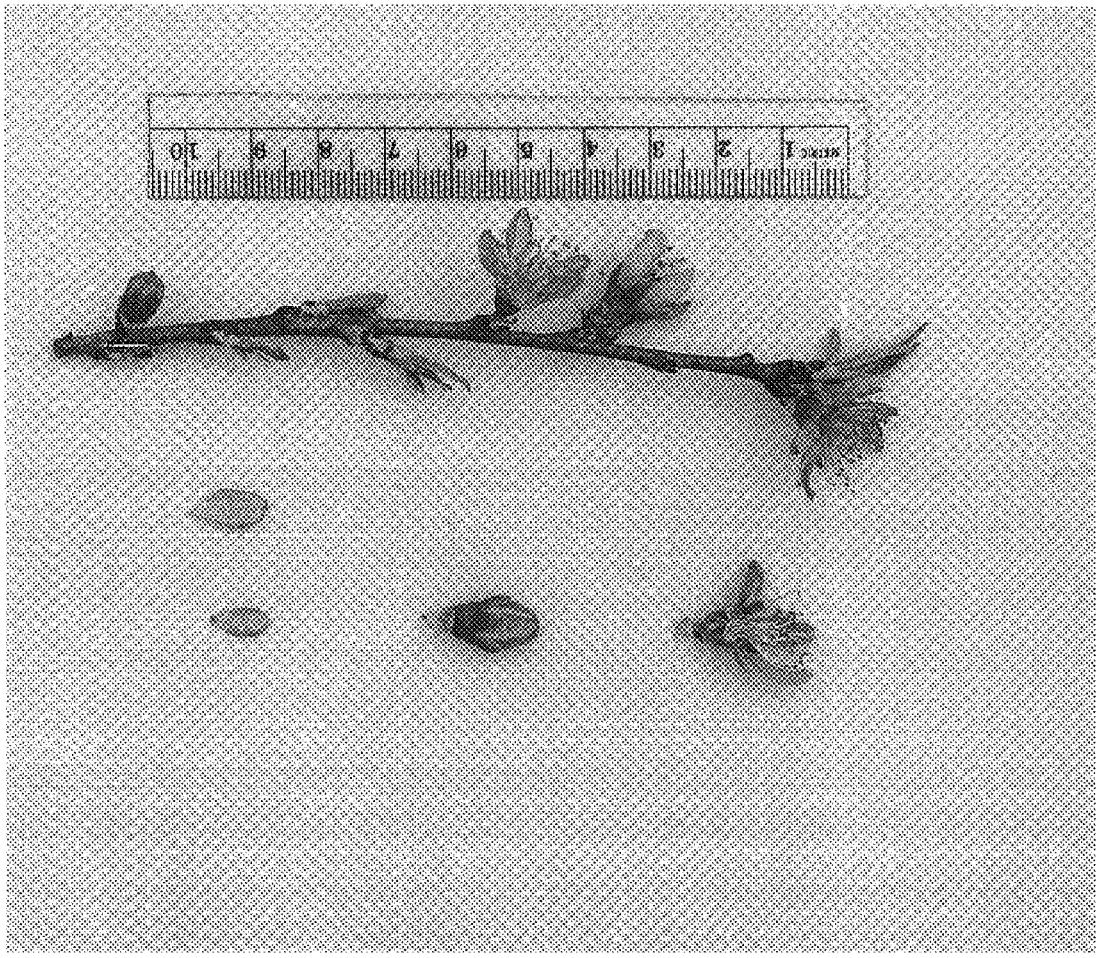
FIG. 3 is a color photograph of a characteristic twig that illustrates the typical flower buds and small, nonshowy flowers of 'NJ352' observed on a tree in Cream Ridge, N.J. on Apr. 21, 2004.
Figure 4:
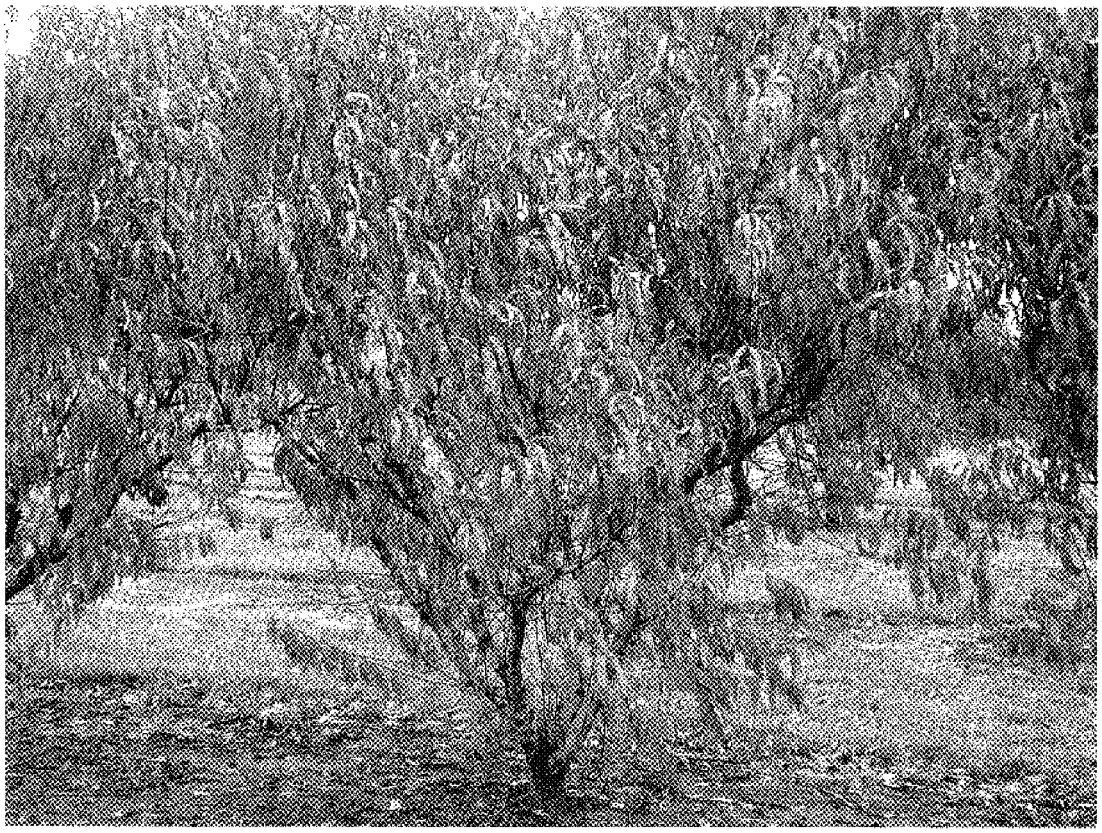
FIG. 4 is a color photograph of a tree of 'NJ352' in early fall that illustrates the spreading growth habit of a tree in Cream Ridge, N.J. on Oct. 27, 2005.
Figure 5:
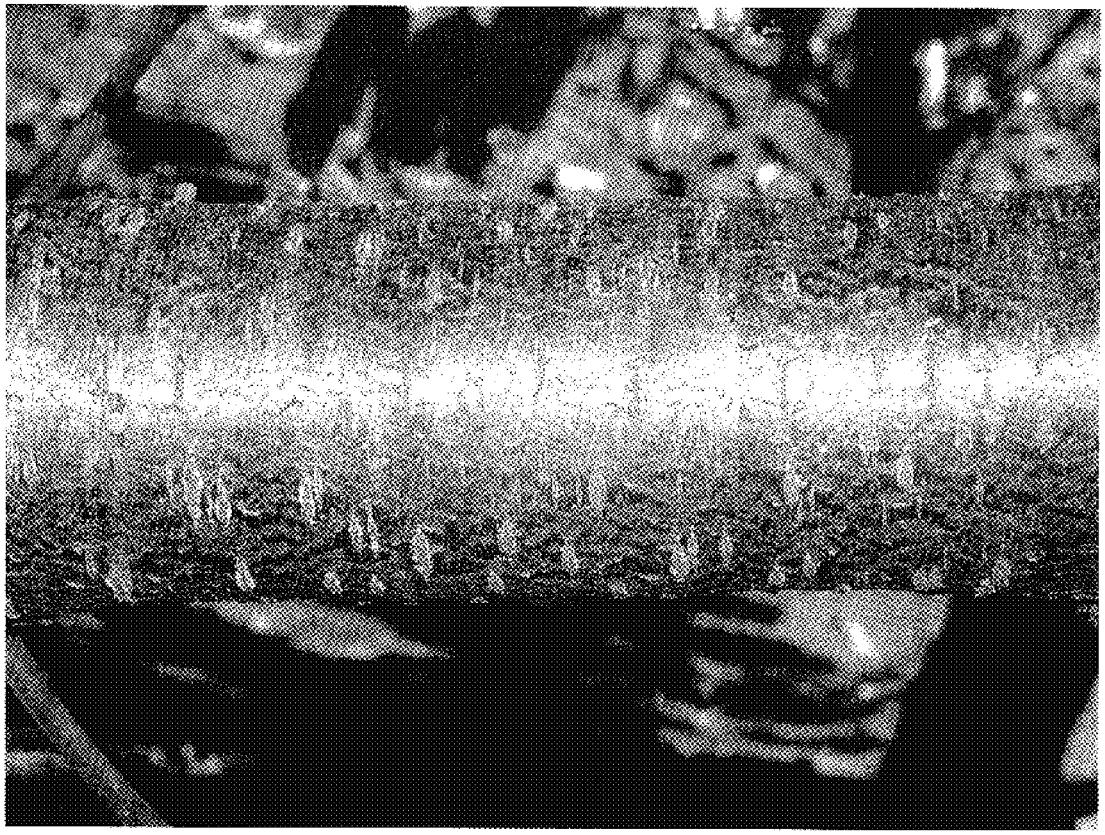
FIG. 5 is a color photograph taken on Oct. 27, 2005 of immature bark of 'NJ352' that illustrates color and the moderate density of grey-white bordered, elliptical lenticels on the immature bark.
Figure 6:
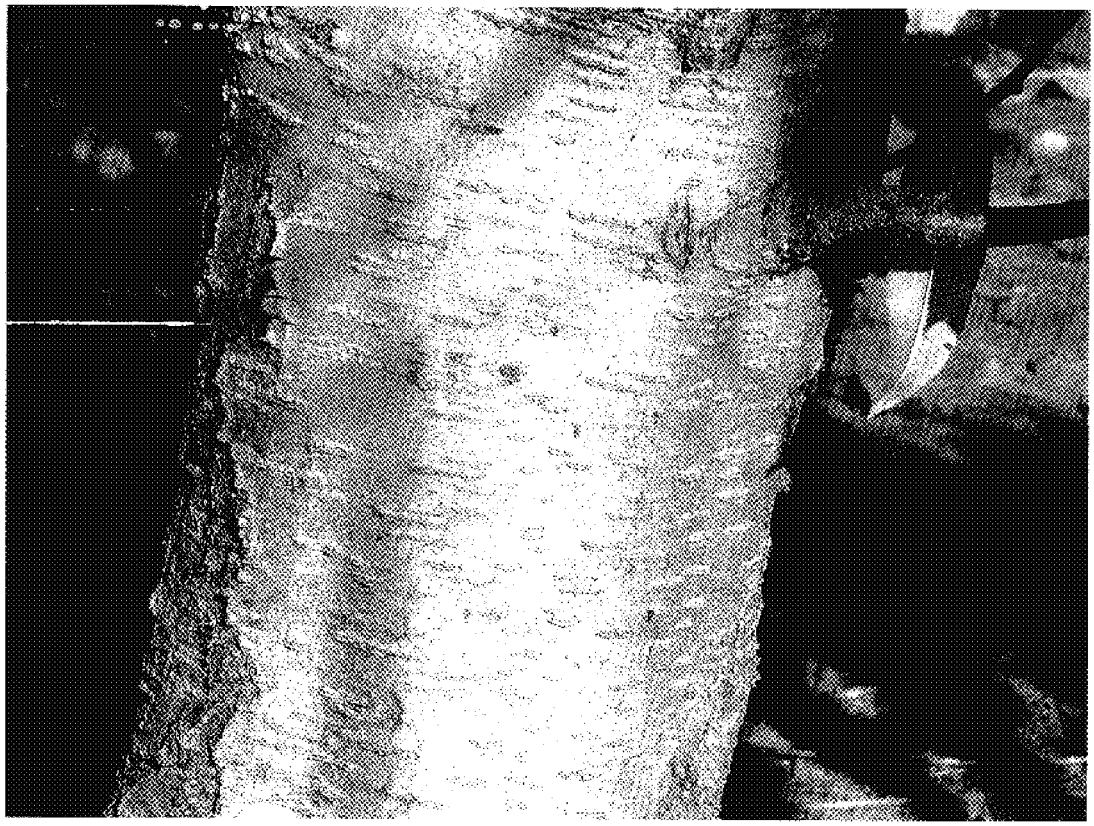
FIG. 6 is a color photograph taken on Oct. 27, 2005 of mature bark of 'NJ352' that illustrates the fairly smooth texture and inconspicuous lenticels of the mature bark.

The colors of and illustration of this type may vary with lighting and other conditions under which conditions and, therefore, color characteristics of this new variety should be determined with reference to the observations described herein, rather than from these illustrations alone.

DETAILED BOTANICAL DESCRIPTION

The following detailed description of the 'NJ352' variety is based on observations of an asexually reproduced tree. The observed tree was six years of age and growing on 'Lovell' seedling rootstock (unpatented) in Research Block C at the Rutgers Fruit Research and Extension Center in Cream Ridge, N.J.

Scientific name: *Prunus persica* L.
Parentage:

| | |
|---|---|
| Seed parent: | D90-9. |
| Pollen parent: | NJ318. |

Tree:

| | |
|---|---|
| Vigor: | Vigorous. |
| Plant hardiness zone: | Growth of plants has only been observed in zone 6b. |
| Dormant flower bud cold tolerance: | At least to −15° C. |
| Overall shape: | Spreading. |
| Height: | Average as compared to other peach cultivars. For example, measurement of a typical grafted tree on 'Lovell' seedling rootstock (unpatented) at six years after planting shows an average height of 4.3 meters when grown in Cream Ridge, New Jersey. |
| Width: | Average as compared to other peach cultivars. For example, measurement of a typical grafted tree on 'Lovell' seedling rootstock (unpatented) at six years after planting shows an average width of 5.2 meters when grown in Cream Ridge, New Jersey. |
| Caliper: | Six year old tree is 48 cm in circumference measured at 20 cm from the ground. |
| Pollination requirements: | Self-pollinating |

Trunk and branches:

| | |
|---|---|
| Trunk bark texture: | Fairly smooth with inconspicuous lenticels becoming rough as the tree ages. |
| Trunk bark color: | Greyed-white (RHS 156c). |
| Primary branches: | Branches that are approximately 15 cm in circumference are greyed-orange (RHS 177a) in color, overlaid with greyed-white (RHS 156c). |
| Lenticels: | Moderate density, approximately 2 per square cm; elliptical shape; typical examples of which measured 6 mm in length and 2.5 mm in width; greyed-orange (RHS 167b) in color and bordered with greyed-white (RHS 156d). |

-continued

| | |
|---|---|
| Branch pubescence: | None. |
| New growth bark: | Color greyed-purple (between RHS 183a and RHS 183b) in sun; color yellow-green (between RHS 152b and RHS 152d) in shade. |
| Internodes: | Length averaging 29.2 mm on a one-year shoot. |

Leaves:

| | |
|---|---|
| Texture: | Glabrous. |
| Sheen: | Young leaves semi-glossy with a flat finish on the underside. |
| Length: | About 167 mm to 190 mm, averaging about 174 mm including the petiole. |
| Width: | About 34 mm to 46 mm, averaging about 39 mm. |
| Petiole: | Averaging 10.6 mm long and about 1.5 mm in diameter. |
| Margin: | Serrulate. |
| Margin undulation: | Slight. |
| Form: | Elliptic. |
| Apex: | Acuminate, curved downward. |
| Base: | Cuneate. |
| Venation: | Pinnate. |
| Glands: | |
| Number: | About 2 to 6, averaging about 3.3. |
| Position: | Located primarily on the leaf margin. |
| Size: | Length averaging 1.1 mm and width averaging 0.9 mm. |
| Form: | Reniform. |
| Stipules: | None observed on mature leaves. |
| Leaf Color: | |
| Upper leaf surface: | Yellow-green (RHS 146a). |
| Lower leaf surface: | Yellow-green (between RHS 147b and RHS 147c). |
| Vein: | Greyed-yellow (between RHS 160b and RHS 160c). |
| Pubescence: | None. |

Flowers:

| | |
|---|---|
| Size: | Small size, typical flower measuring between 12.4 mm to 17.8 mm, averaging about 15.5 mm across. |
| Color: | |
| Dormant bud: | Grey (between RHS 201a and RHS 201d). |
| Pink stage bud: | Red (between RHS 54b and RHS 62c). |
| Open flower: | Young open flowers red (between RHS 55b and RHS 55c), with red venation (between RHS 55a and RHS 55b) at petal fall. |
| Petals: | Typically five petals per flower; cupped and obovate in shape; averaging about 11.0 mm long and 7.9 mm wide. Red (between RHS 55b and RHS 55c) in color. |
| Petal apex: | Obtuse. |
| Petal base: | Cuneate. |
| Stamens: | |
| Number: | Variable, typical range 36 and 40, averaging 38. |
| Length: | Variable, between 9.4 mm to 11.3 mm, averaging 10.5 mm. |
| Filament color: | Green-white (RHS 157c). |
| Anther color: | Red (RHS 53a). |
| Pistil: | |
| Number: | One. |
| Size: | Length between 15.8 and 17.1 mm, averaging about 16.5 mm. |
| Pistil color: | Greyed-yellow (RHS 160a). |
| Ovary: | Dense pubescence and ellipsoid in shape. |

-continued

Sepals:

| | |
|---|---|
| Number: | Five. |
| Pubescence: | Short and light density. |
| Color: | Yellow-green (RHS 152b) with a greyed-red (RHS 182b) over color. |
| Shape: | Triangular, with a rounded apex. |
| Size: | Length averaging 4.3 mm, width averaging 3.5 mm. |
| Nectar cup color: | Greyed-orange (between RHS 167a and RHS 168b). |
| Pollen: | Abundant; yellow (RHS 11a) in color. |
| Fragrance: | Very slight. |
| Bloom season: | Onset of bloom in 2004 on April 16; full bloom on April 18. |

Fruit:

| | |
|---|---|
| Size: | Large, averaging about 7.3 cm long, 7.1 cm wide parallel to the suture and 7.3 cm wide perpendicular to the suture. |
| Typical weight: | 210 g. |
| Form: | |
| Longitudinal section: | Round. |
| Traverse section: | Nearly round, one side of suture may tend to be slightly lipped is some years. |
| Suture: | Very shallow, extending from the base to apex. |
| Ventral surface: | Typically smooth, slightly lipped in some years. |
| Base: | Round. |
| Apex: | Round, apex point may be slightly depressed. |
| Stem: | Average length of 7.1 mm and an average diameter of 5.9 mm. |
| Skin: | |
| Thickness: | Average. |
| Surface: | Regular with short pubescence. |
| Tenacity: | Average. |
| Astringency: | None. |
| Tendency to crack: | Low. |
| Color: | Mottled greyed-red (RHS 181a) over an orange-red (RHS 24b) blush; ground color yellow-orange (RHS 16a). |

Fruit Properties:

| | |
|---|---|
| Flesh color: | Yellow-orange (RHS 16b). |
| Flesh adhesion: | Freestone. |
| Juice: | Moderate. |
| Texture: | Firm, but melting. |
| Fibers: | Not noticeable. |
| Ripens: | Between August 13 and August 29 at Cream Ridge, New Jersey. |
| Flavor: | Average to above average, moderately acidic. |
| Soluble solids: | 10.4%. |
| Aroma: | Very slight. |
| Eating quality: | Good. |

-continued

| | |
|---|---|
| Keeping quality: | Average. Has held its flavor and firmness for at least 7 days in cold storage at 1° C. to 4° C. |
| Shipping quality: | Very good. Fruit are generally very firm at harvest. No bruising or scaring disorders have been observed. |
| Usage: | Dessert. |
| Market: | Local and long distance. |
| Productivity: | Good. Trees have produced a crop in 5 out of 7 years and a full crop in 5 out of 7 years at Cream Ridge, New Jersey. |

Stone:

| | |
|---|---|
| Type: | Freestone. |
| Form: | Obovoid. |
| Base: | Narrow. |
| Apex: | Narrow. |
| Surface: | Pit grooves. |
| Ventral suture: | Small to medium, truncated at the apex. |
| Dorsal ridge: | Low, narrow, and fine lines. |
| External color: | Greyed-orange (between RHS 174a and RHS 174b) overlaid with greyed-purple (RHS 183c). |
| Internal color when cracked: | Greyed-orange (between RHS 165c and RHS 165d). |
| Cavity surface color: | Greyed-orange (RHS 165c). |
| Average stone dry weight: | 5.2 g. |
| Average stone wall thickness: | Varies between 3.9 and 9.5 mm. |
| Size: | Averages about 35 mm long, 24 mm wide parallel to the dorsal ridge, and 17 mm wide perpendicular to the dorsal ridge. |
| Tendency to split: | Low. |

Kernel:

| | |
|---|---|
| Form: | Ovate. |
| Skin color: | Greyed-orange (RHS 164a). |
| Vein color: | Greyed-orange (between RHS 165a and RHS 165b). |
| Viability: | Yes. |
| Size: | Averages about 21 mm long, 12.6 mm wide, and 5.4 mm in breadth. |

Plant/fruit disease and pest resistance/susceptibility: No atypical resistances/susceptibilities have been noted under normal cultural practices.

We claim:

1. A new and distinct variety of peach tree, substantially as herein shown and described.

* * * * *